(12) United States Patent  (10) Patent No.: US 6,592,589 B2
Hajianpour  (45) Date of Patent: Jul. 15, 2003

(54) DEVICE AND METHOD FOR PLUGGING A BONE CHANNEL WITH AN EXPANDABLE MEDULLARY PLUG

(76) Inventor: Mohammed Ali Hajianpour, 1706 Vestal Dr., Coral Springs, FL (US) 33071

( * ) Notice: Subject to any disclaimer, the term of this patent is extended or adjusted under 35 U.S.C. 154(b) by 207 days.

(21) Appl. No.: 09/730,972

(22) Filed: Dec. 6, 2000

(65) Prior Publication Data

US 2002/0068981 A1 Jun. 6, 2002

(51) Int. Cl.⁷ .................................................. A61F 2/30
(52) U.S. Cl. ........................................ 606/95; 623/23.48
(58) Field of Search ........................... 606/95; 623/23.48

(56) References Cited

U.S. PATENT DOCUMENTS

| 4,276,659 A | * | 7/1981 | Hardinge | |
| 4,447,915 A | * | 5/1984 | Weber | |
| 4,523,587 A | * | 6/1985 | Frey | |
| 4,625,722 A | * | 12/1986 | Murray | |
| 4,627,434 A | * | 12/1986 | Murray | |
| 4,697,584 A | | 10/1987 | Haynes | 606/95 |
| 4,745,914 A | * | 5/1988 | Frey et al. | |
| 5,059,193 A | * | 10/1991 | Kuslich | |
| 5,092,891 A | * | 3/1992 | Kummer et al. | |
| 5,383,932 A | | 1/1995 | Wilson et al. | 623/16 |
| 5,662,657 A | * | 9/1997 | Carn | |
| 5,766,178 A | | 6/1998 | Michielli et al. | 606/95 |
| 5,782,917 A | | 7/1998 | Carn | 623/16 |
| 5,827,289 A | | 10/1998 | Reiley et al. | 606/86 |
| 5,849,014 A | | 12/1998 | Mastrorio et al. | 606/94 |
| 5,861,043 A | | 1/1999 | Carn | 623/16 |
| 5,879,403 A | | 3/1999 | Ostiguy et al. | 623/22 |
| 5,935,169 A | | 8/1999 | Chan | 623/16 |
| 5,972,034 A | | 10/1999 | Hoffmann et al. | 623/23 |
| 5,997,580 A | | 12/1999 | Mastrorio et al. | 623/22 |
| 6,227,860 B1 | * | 5/2001 | Hobo | |
| 6,251,141 B1 | * | 6/2001 | Pierson, III et al. | |

FOREIGN PATENT DOCUMENTS

WO   WO 00/28926   *   5/2000

* cited by examiner

*Primary Examiner*—Ralph A. Lewis
(74) *Attorney, Agent, or Firm*—Ronald V. Davidge

(57) ABSTRACT

A plug for stopping the flow of bone cement in a bone channel, such as the intramedullary bone canal, or a previously prepared channel, includes an actuator and a number of flexible beams extending around the bone plug. The actuator is removably attached to a rod within an insertion tool used to deploy the bone plug at a predetermined location within the channel. Within the tool, the rod is pulled to move the actuator into a position applying a compressive force to act between the ends of each of the flexible beams. This compressive force causes each beam to buckle outward, into contact with the channel. The rod is then released from the actuator, and the tool is withrawn from the channel so that bone cement can be applied to hold a prosthesis in place within the channel in a proximal direction from the bone plug.

17 Claims, 3 Drawing Sheets

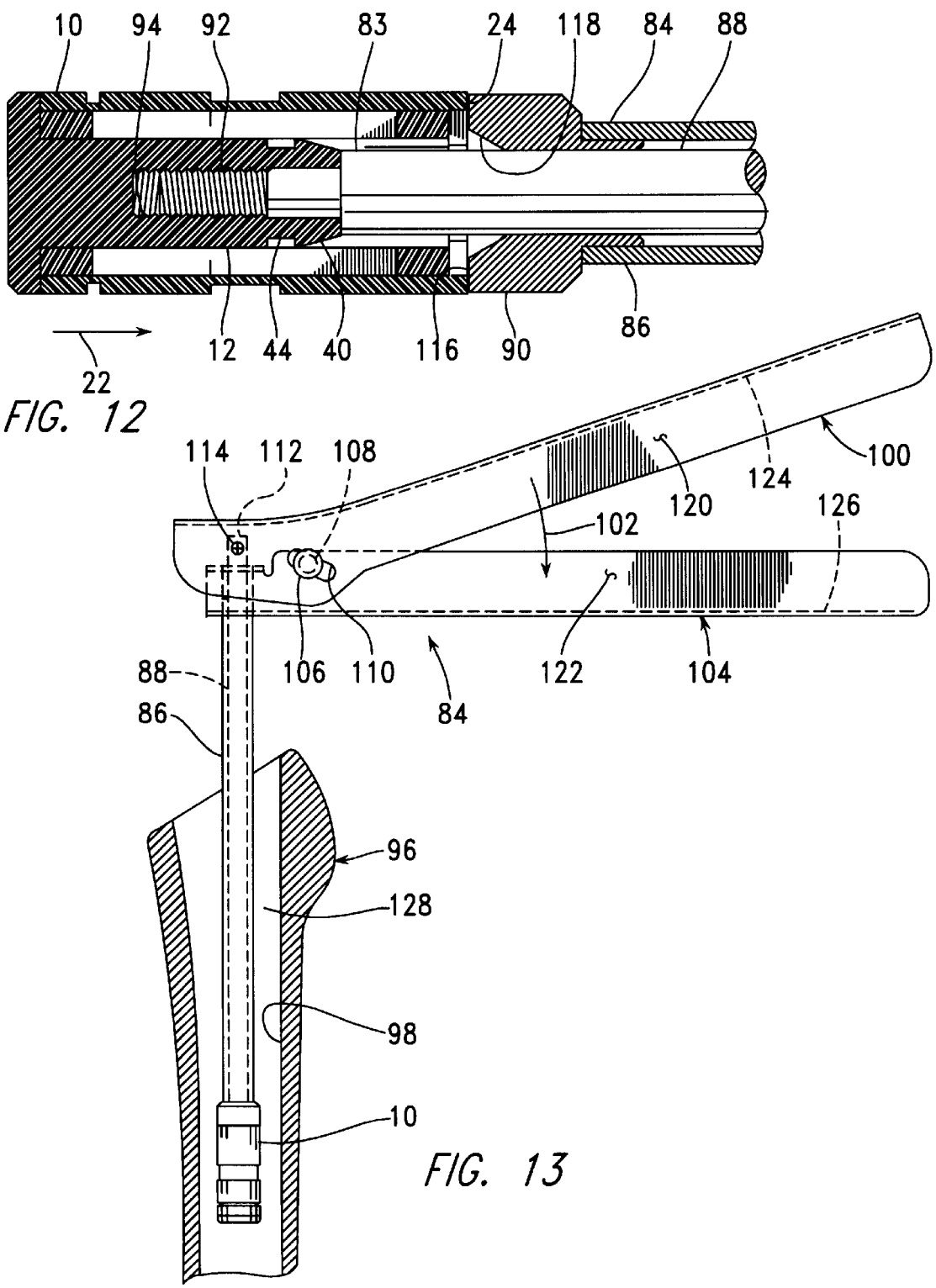

DEVICE AND METHOD FOR PLUGGING A BONE CHANNEL WITH AN EXPANDABLE MEDULLARY PLUG

CROSS REFERENCE TO A RELATED APPLICATION

This application is related to U.S. application Ser. No. 09/590,039, now U.S. Pat. No. 6,506,194, entitled "Medullary Plug Including an External Shield and an Internal Valve," having common inventorship with the present invention, the disclosure of which is hereby incorporated herein by reference.

BACKGROUND INFORMATION

1. Field of Invention

This invention relates to medical apparatus for use in the implantation of a joint prosthesis to the end of a bone and, more particularly, to a plug for stopping the flow of bone cement, used in the attachment of a prosthesis, at a predetermined point within the intramedullary bone canal or previously prepared channel within the bone.

2. Description of the Related Art

A number of U.S. Patents describe apparatus for plugging the open end of an intramedullary bone canal to restrict the flow of bone cement during the insertion of bone cement, particularly during the pressurized injection of such a cement during an operative procedure involving the fixation of the stem of an artificial joint prosthesis to the end of a bone such as in the fixation of a hip joint prosthesis to the proximal femur.

For example, U.S. Pat. No. 5,935,169 describes a bone cement plug including a core having a substantially cylindrically-shaped base portion defining a threaded bore therein extending axially and distally from a proximal end of the base portion; a first leg portion depending from and extending distally from the base portion; and a second leg portion depending from and extending distally from the base portion and opposed to the first leg portion; the base portion threaded bore being adapted to receive an expander screw to wedge apart the first and second leg portions, whereby to expand the core widthwise to secure the plug in the bone canal; and the expander screw, the screw comprising a generally cylindrically-shaped body having a tapered distal end, and a proximal end in which is disposed a threaded bore, external threads disposed on the body, and an annular flange extending outwardly from the proximal end of the body, the screw being threadedly engageable with the core threaded bore for advancement of the screw into the plug for the wedging apart of the first and second legs. A method is also disclosed for using the bone cement plug to compact bone cement into a bone canal during total joint replacement surgeries. However, this type of bone cement plug, having a finite number, such as two, mechanically coupled legs to expand and structures shaped as partial disks for contacting the bone channel, is limited in its flexibility in terms of an ability to compensate for differences in the diameter of various bone channels into which the plug may be inserted. What is needed is a bone plug having a larger number of relatively flexible contact surfaces extending around the bone plug to make contact with the channel.

A number of patents describe bone plugs including a central core from which a number of disks extend as fins at spaced locations. Examples of such devices are found in U.S. Pat. Nos. 5,383,932, 5,662,657, 5,766,178, 5,782,917, 5,861,043, 5,879,403. Such systems allow only deformation of the individual disks to compensate for changes in the shape of the bone channel, such as out-of-round conditions and changes in hole diameter. Again, what is needed is a bone plug having a larger number of relatively flexible contact surfaces extending around the bone plug to make contact with the channel. Also, what is needed is a way of deploying these contact surfaces to make contact with the channel only after the bone plug is moved into place, so that the bone plug can be easily moved into the desired position, without having to overcome significant dragging forces.

U.S. Pat. No. 4,697,584 describes an inflatable bone plug which is inflated with a fluid capable of escaping from the plug within a relatively short period of time after the bone cement holding the prosthesis in place has hardened to avoid possible weakening of the cortical bone surrounding the inflated plug. This invention also relates to an inflatable bone plug of the above type which is preferably constructed from a silicone elastomer and is pressurized with carbon dioxide gas. However, for substantial inflation to occur in the desired manner, the bone plug is made of an elastomeric material. Such materials, which have elastic properties allowing substantial elongation, are subject to cutting and puncturing due to bone splinters and sharp edges in a channel cut into bone, as the plug is moved into position within the channel. Furthermore, the use of an internal valve associated with a needle for injecting a fluid complicates the manufacture of the inflatable bone plug.

U.S. Pat. No. 5,849,014 describes a cement restrictor system including an inflatable body, a conduit having first and second ends that defines a fluid passage to and from the inflatable body, and a shield releasably securable to the conduit. In an exemplary method of making a cement plug with the system an obstruction, such as the shield, is placed in a medullary canal of a long bone beyond the isthmus of the long bone. The obstruction is held in place with the inflatable body. A predetermined quantity of bone cement is poured into the medullary canal and localized by the obstruction. The bone cement is allowed to harden; and the conduit and inflatable body are removed from the bone. Again, the inflatable body is elastomeric and is not protected from cutting or puncturing by bone splinters and sharp edges as the restrictor system is moved into place within a bone channel, with the inflatable body preceding the shield. Also, the separate formation of a bone plug from cement and subsequent removal of the conduit and inflatable body to allow insertion of the prosthesis may lengthen the time required for a hip replacement procedure.

U.S. Pat. No. 5,997,580 describes a cement restrictor including a member or body that is expandable or transitionable from a first diameter to a second diameter. The cement restrictor includes a single or multiple finned body having a first stable state and a second stable state. In the first stable state, the cement restrictor is narrower than in the second stable state. While the cement restrictor is readily transitionable from the first stable state to the second stable state, the transition can be irreversible. An illustrative embodiment of the cement restrictor includes a body having a first end and a second end. Bistable fins extend radially from the body and are irreversibly movable from a first stable state to a second stable state. The fins are concave with respect to the first end of the body in the first stable state and convex with respect to the first end of the body in the second stable state. The diameter of each fin is larger in the second stable state than in the first stable state. Other embodiments of inventive cement restrictors are shown that include shape memory material that changes shape or dimension(s) in response to temperature and/or stress.

However, the expansion of the cement restrictor is limited to the transition between the first stable state and the second stable state, together with elastic and plastic deformation of the material. This method thus does not offer the kind of flexibility of a system with an inflatable body in expansion to meet varying conditions within the bone channel. Furthermore, the time required to apply liquids at different temperatures to make the transitionable body perform as desired may increase the time required for hip replacement surgery.

SUMMARY OF THE INVENTION

It is a first objective of the present invention to provide a medullary bone plug which can be easily inserted to a point for deployment in a channel within bone and expanded to fit within the channel, to block a subsequent flow of bone cement within the channel, beyond the bone plug, as bone cement is used to fasten a prosthesis in place.

It is a second objective of the present invention to provide a medullary bone plug which expands to fill a bone channel having a diameter within a range of diameters.

It is a third objective of the present invention to provide a medullary bone channel which expands to provide stable attachment to surfaces within a bone channel.

In accordance with a first aspect of the present invention, a bone plug is provided for plugging a channel within a bone to stop of flow of bone cement through the channel. The bone plug includes a number of flexible beams, an actuator, and a latch. The flexible beams extend around a periphery of the bone plug between first and second end portions of the bone plug. The actuator is movable between a disengaged position and an engaged position. Movement of the actuator from the disengaged position to the engaged position applies a compressive force acting between opposite ends of each flexible beam causing the flexible beam to buckle outward. The latch holds the actuator in the engaged position.

In accordance with a second aspect of the present invention, there is provided apparatus including a bone plug as described above, and an insertion tool having a frame and a rod. The rod, which is movable within the frame and removably attached to the actuator, moves the actuator in a first direction from the disengaged position to the engaged position, before releasing the actuator, as the second end portion of the bone plug is held in contact with the frame of the insertion tool.

In accordance with a third aspect of the present invention, there is provided a process for plugging a channel within a bone at a predetermined level within the channel to stop a flow of bone cement through the channel. The process includes attaching a bone plug to a distal tip of an insertion tool, inserting the bone plug attached to the insertion tool to the predetermined level within the channel, pulling a rod within the insertion tool to cause the bone plug to expand within the channel into contact with the channel, releasing the bone plug from the insertion tool, and withdrawing the insertion tool from the channel.

BRIEF DESCRIPTION OF THE DRAWINGS

FIG. 12 is a longitudinal cross-sectional view of the medullary bone plug of FIG. 1, removably attached to a tip of an insertion tool, FIG. 13 is a longitudinal cross-sectional view of a femur having a previously-prepared channel, showing the insertion therein of the medullary bone plug of FIG. 1, using the insertion tool of FIG. 12.

DESCRIPTION OF THE INVENTION

Figure 1:
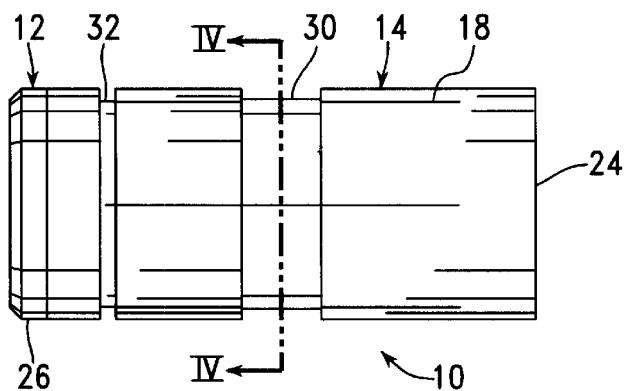
FIG. 1 is a side elevation of an expandable medullary bone plug built in accordance with the present invention in an unexpanded condition.
Figure 2:
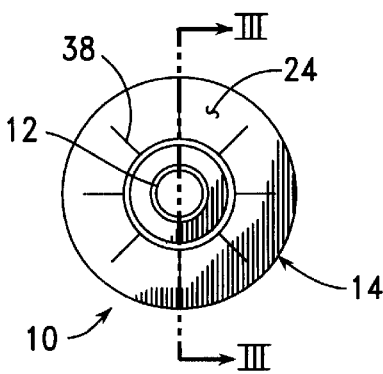
FIG. 2 is a proximal end elevation of the medullary bone plug of FIG. 1.
Figure 3:
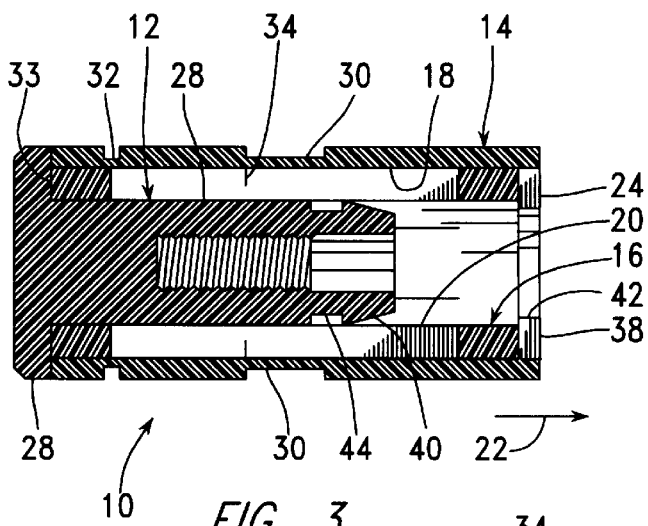
FIG. 3 is a longitudinal cross-sectional view of the medullary bone plug of FIG. 1, taken as indicated by section lines III—III in FIG. 2.
Figure 4:
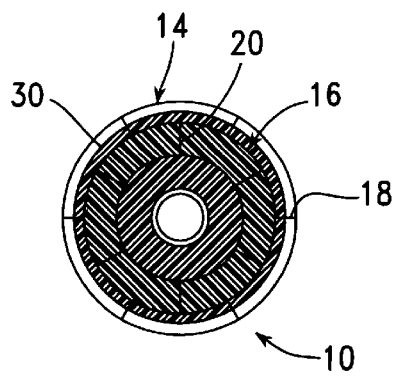
FIG. 4 is a transverse cross-sectional view of the medullary bone plug of FIG. 1, taken as indicated by section lines IV—IV in FIG. 1.

FIGS. 1–4 show an expandable medullary bone plug, generally indicated as 10, built in accordance with the present invention, in its initial, unexpanded condition, with FIG. 1 being a side elevation thereof, with FIG. 2 being a proximal end view thereof, with FIG. 3 being a longitudinal cross-sectional view thereof, taken as indicated by section lines III—III in FIG. 2, and with FIG. 4 being a transverse cross-sectional view thereof, taken as indicated by section lines IV—IV in FIG. 1.

The medullary bone plug 10 includes an actuator 12, an outer sleeve 14, and an inner sleeve 16 extending within the outer sleeve 14. The central portion of the outer sleeve 14 is divided into six outer flexible beams 18, while the central portion of the inner sleeve 16 is similarly divided into six inner flexible beams 20. The outer and inner flexible beams 18, 20 extend parallel to one another in the longitudinal direction of arrow 22. The outer sleeve 14 also includes an inward-extending proximal end cap portion 24. The actuator includes an outward-extending distal head portion 26 and a shaft portion 28 extending within the inner sleeve 16. Each of the outer flexible beams 18 preferably includes a central section 30 having a reduced thickness and a groove 32 near an end of the outer flexible beam 18. The actuator 12 and the sleeves 14, 16 are preferably composed of a high-density polyester, which provides sufficient flexibility to allow for expansion in a manner to be described, and which is safe for use in the intended application.

As shown particularly in FIG. 4, the outer sleeve 14 and the inner sleeve 16 are preferably held in a rotational relationship causing the center of each inner flexible beam 20 to extend below a gap between adjacent outer flexible beams 18. This may be achieved by bonding the outer and inner sleeves 14, 16 to one another near an end 33 of the sleeves, or by fitting the sleeves together with mating notches, keys, etc. Such a bonding process may be ultrasonic or adhesive.

Figure 5:
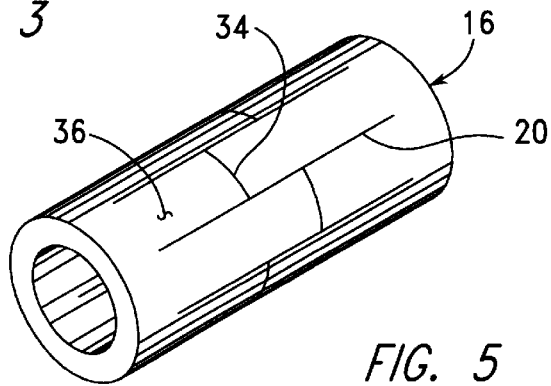
FIG. 5 is an isometric view of an inner sleeve within the medullary bone plug of FIG. 1.

FIG. 5 is an isometric view of the inner sleeve 16, showing the division of a central portion of this inner sleeve 16 into six inner flexible beams 20. As shown in FIGS. 3 and 5, each of these inner flexible beams 20 is preferably split by a narrow groove 34 extending transversely across the outer surface 36 of the inner flexible beam 20 to a depth approximately half way through the thickness of the inner flexible beam 20. Preferably, the grooves 34 of alternate inner flexible beams are offset toward opposite ends of the inner sleeve 16.

Figure 6:
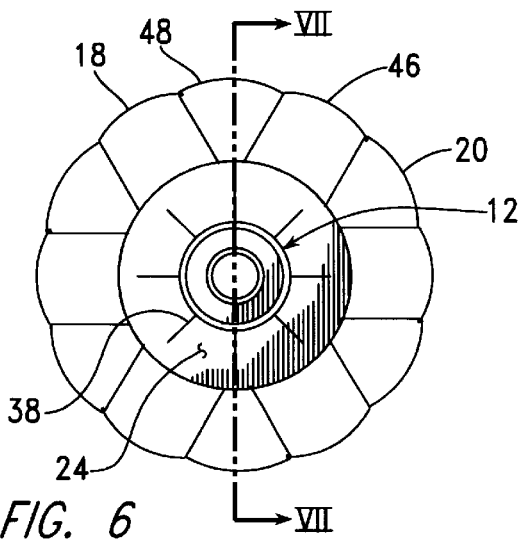
FIG. 6 is a proximal end view of the medullary bone plug of FIG. 1 in a fully expanded condition.
Figure 7:
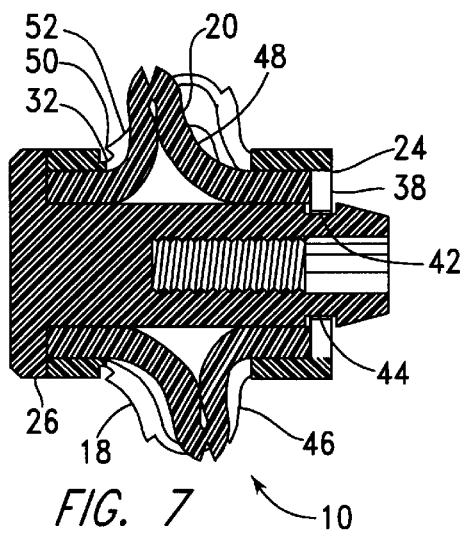
FIG. 7 is a longitudinal cross-sectional view of the expanded medullary bone plug of FIG. 6, taken as indicated by section lines VII—VII therein.

FIGS. 6 and 7 show the expandable medullary bone plug 10 in a fully expanded condition, with FIG. 6 being a proximal end view thereof, and with FIG. 7 being a longitudinal cross-sectional view thereof, taken as indicated by section lines VII—VII in FIG. 6 to show the shape of inner flexible beams 20 in the fully expanded condition. The medullary bone plug 10 is brought into the fully expanded condition of FIGS. 6 and 7 by moving the actuator 12 in the longitudinal direction of arrow 22 relative to the proximal end cap portion 24 of the outer sleeve 28, between the disengaged position, in which it is shown in FIGS. 1–4, and the engaged position, in which it is shown in FIGS. 6 and 7. The proximal end cap portion 24 is divided into a number of inward-extending tabs 38, the ends of which are deflected outward, in the direction of arrow 22, as the tapered proximal end 40 of the actuator 40 moves through a hole 42 at the ends of the tabs 38. As the tapered proximal end 40 is moved past the tabs 38, the ends of these tabs 38 return, opposite the direction of arrow 22, to remain in a latching groove 44 of the actuator 12. In this way, the tabs 38 act together as a latch to prevent the return movement of the actuator 12 from its engaged position.

Moving the actuator 12 from its disengaged position to its engaged position shortens the distance between the outward-extending distal head portion 26 of the actuator 12 and the proximal end cap portion 24 of the outer sleeve 28, causing both the outer flexible beams 18 and the inner flexible beams 20 to buckle outward. Since the outer sleeve 14 and the inner sleeve 16 are held in a rotational relationship causing the center of each inner flexible beam 20 to extend below a gap between adjacent outer flexible beams 18, as explained above in reference to FIG. 4, and since central portions 46 of adjacent outer flexible beams 18 separate from one another as these beams 18 buckle outward, central portions 48 of the inner flexible beams 20 move outward between the central portions 46 of adjacent outer flexible beams during the buckling process. In this way, the flexible beams 18, 20 are spread to block the flow of bone cement within a channel.

Each of the grooves 32 near a distal end of an outer flexible beam 20 shifts a pattern of axial stresses, caused by the movement of actuator 12, within the flexible beam 20 inward, while providing a gap into which an edge 50 of the outer surfaces 52 of the beam can move, promoting the outward buckling movement of the beam.

Figure 8:
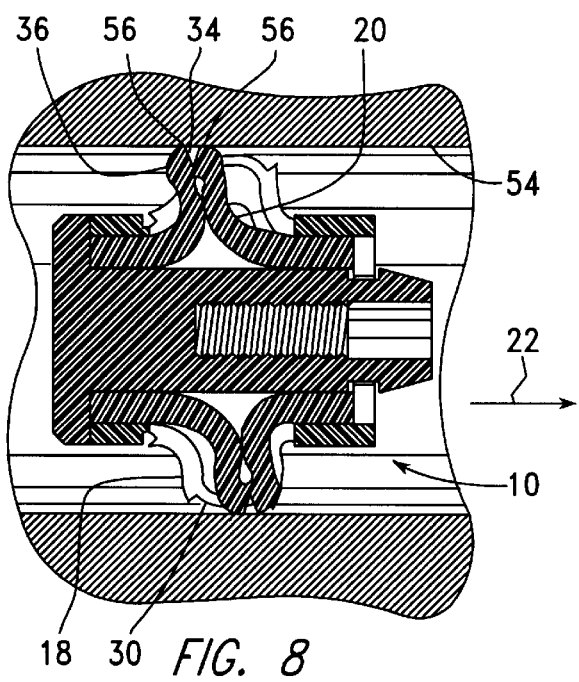
FIG. 8 is a longitudinal cross-sectional view of the expanded medullary bone plug of FIG. 1, in a partly expanded condition within a bone channel.

FIG. 8 is a longitudinal cross-sectional view of the expandable bone plug 10 in a partly expanded condition within a bone channel 54. This figure is representative of the bone plug 10 as applied within a bone channel 54 to stop the flow of bone cement. The bone plug 10, in its fully expanded condition, as shown in FIGS. 6 and 7, must be larger than the diameter of the bone channel 54, so that the bone plug 10, being blocked from reaching its fully expanded condition by the bone channel 54, exerts a force on the channel 54, blocking the flow of bone cement around the bone plug 10 and holding the bone plug 10 in position within the channel 54.

In each of the inner flexible beams 20, the thin groove 34 widens with the deflection of the beam 20 from the unexpanded condition, so that edges 56, at the intersections of the outer surface 30 of the beam 20 and the groove 34, are directed outward into the surface of the bone channel 54. These edges 56 form lines along which pressure is exerted between the inner flexible beams 20 and the bone channel 54. Since the thin grooves 34 are offset in alternating beams 20, in the manner discussed above in reference to FIG. 5, the areas of contact between the beams 20 and the bone channel 54 are spread apart in the longitudinal direction of arrow 22, giving the bone plug 10 stability in the prevention of twisting in, for example, the direction of arrow 58.

The reduction in thickness of the central section 30 of each outer flexible beam 18 provides a local increase in flexibility of this beam which initially promotes deflection of the outer flexible beams 18 as the actuator 12 is moved from its disengaged position, as shown in FIG. 3. Then, after contact is made between the outer flexible beam 18 and the bone channel 54, the increased flexibility of the central section 30 allows a greater length of this central section 30 to conform to the surface of the bone channel 54, aiding in stopping the flow of bone cement.

Figure 9:
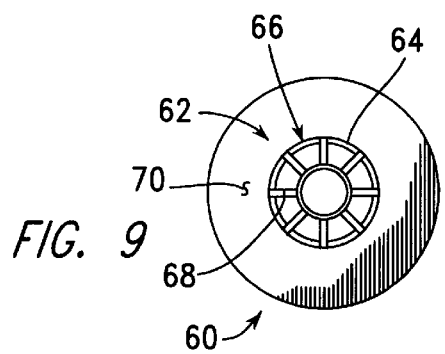
FIG. 9 is a proximal end view of an expandable medullary bone plug in an unexpanded condition, showing an alternative latching mechanism.

FIG. 9 is a proximal end view of an expandable medullary bone plug 60 in an unexpanded condition, showing an alternative latching mechanism 62, in which the proximal end 64 of the actuator 66 is split into a number of sections 68, which move inward as the proximal end 64 moves through a hole, not shown, in an end cap 70, which is not divided into individual tabs 38, as explained above, and as shown in FIG. 2. The medullary bone plug 60 is otherwise similar to the medullary bone plug 10 described above.

Figure 10:
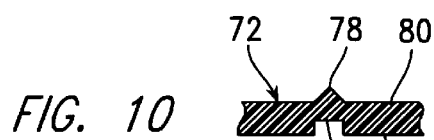
FIG. 10 is a fragmentary longitudinal cross-sectional view of a flexible beam within a medullary bone plug, showing an alternative method for providing a contact surface, shown with the medullary bone plug in an unexpanded condition.
Figure 11:
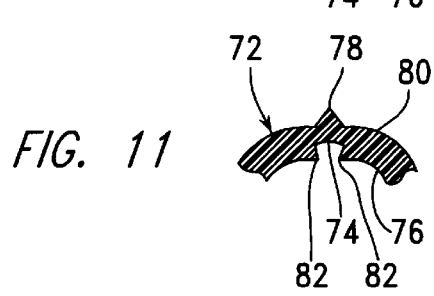
FIG. 11 is a fragmentary longitudinal cross-sectional view of the flexible beam of FIG. 10, shown with the medullary bone plug in a partly expanded condition.

FIGS. 10 and 11 are fragmentary longitudinal cross-sectional views of an alternative inner flexible beam 72 within a medullary bone plug otherwise similar to the medullary bone plug 10, described above, showing an alternative method for providing a surface for contacting the bone channel 54 (shown in FIG. 8). FIG. 10 shows the inner flexible beam 72 in an undeflected condition, with the medullary bone plug in an unexpanded condition, while FIG. 11 shows the inner flexible beam 72 in a deflected condition, with the medullary bone plug in a partly expanded condition. The alternative inner flexible beam 72 includes a wide groove 74, extending along an internal surface 76 opposite a rib 78, extending outward from an external surface 80. Like the grooves 34, the grooves 74 extend transversely across the inner flexible beams, with grooves 74 on adjacent beams being preferably offset in alternating longitudinal directions, as particularly shown in FIG. 3. As deflection occurs with buckling of the beam 72, as shown in FIG. 11, the edges 82 formed by the intersection of the groove 74 with the internal surface 76 of the beam 72 move into the space provided by the groove 74. As the buckling movement of the beam 72 continues, the outer edge of the rib 78 is brought into contact with the bone channel 54, causing the medullary bone plug to be held in place and stopping the flow of bone cement.

In this way, a relatively wide groove, such as groove 74 promotes the buckling of a beam in a direction allowing the edges of the groove to move into the space within the groove. On the other hand, the grooves 34, described above particularly in reference to FIGS. 3 and 5, which extend into the inner flexible beams 20 from an outer surface 36, must not be allowed to establish the direction of bending for the beams 20, since these beams must buckle outward at the grooves 34, not inward, to function as described above. For this reason, the grooves 34 must be narrow, preferably being cut into the material of the inner flexible beams 20. In this context, a wide groove is understood to be one wide enough to allow inward movement of the adjacent edges, such as the groove 32, discussed in reference to FIG. 7, and the groove 74, while a narrow groove is one not allowing significant inward movement of the adjacent edges, such as the groove 34.

FIG. 12 is a longitudinal cross-sectional view of the medullary bone plug 10 removably attached to a tip 83 of an installation tool, generally indicated as 84. The installation tool 84 includes a tube 86, a rod 88, and a bushing 90, in which the rod 88 is slidably mounted to extend within the tube 86. The distal end of the rod 88 includes an externally threaded portion 92 mating with an internally threaded hole 94 within the actuator 12 of the medullary bone plug 10.

FIG. 13 is a longitudinal cross-sectional elevation of a femur 96, including a previously-prepared channel 98, showing the insertion therein of the medullary bone plug 10 with the insertion tool 84. The medullary bone plug 10 is lowered within the channel 98 to a position at which its deployment is desired. Next, the rod 88 extending within the tube 86 of the insertion tube 84 is pulled in the direction of arrow 22 by pivoting a movable handle 100 of the insertion tool 84 in the direction of arrow 102 relative to a stationary handle 104. The stationary handle 104 is attached to the tube 86, and the movable handle 100 is pivotally mounted on the stationary handle 104 by means of a pin 106 extending through holes 108 in the stationary handle 104 and through slots 110 in the movable handle 102. The movable handle 100 is also pivotally connected to a proximal end 112 of the rod 88 by means of a pin 114. The elongation of slots 110 allows the rod 88 to move straight within the tube 86 while the movable handle 102 pivots about pin 106.

Referring to FIGS. 12 and 13, and additionally referring to FIG. 8, pulling the rod 66 in the direction of arrow 22 causes the actuator 12, attached to the rod 66, to move between the disengaged position of FIG. 12 and the engaged position of FIG. 8. As this movement occurs, the flexible beams 18 and 20 buckle into the position of FIG. 8, coming into contact with the channel 98 to stop the subsequent flow of bone cement through the channel. During this movement of the actuator 12, the proximal end cap portion 24 of the medullary bone plug 10 is held against the distal end 116 of the bushing 90.

The bushing 90 also includes a restraining surface 118, which engages the tapered proximal end 40 of the actuator 12 to prevent movement of the actuator 12 in the direction of arrow 22 past its engaged position. Thus, continued movement of the rod 88 in this direction causes the threads of the internally threaded hole 94 of the actuator 12 to strip, with the threaded tip portion 92 of the rod being pulled away from the hole 94 to release the medullary bone plug 10 from the insertion tool 84.

The handles 100, 104 are each formed as "U"-shaped structures, with a pair of sides 120, 122 extending in a common direction from an end 124, 126. The sides 122 of the stationary handle 104 extend within the sides 120 of the movable handle 100.

After the bone plug 10 has been released from the insertion tool 84, this tool is removed, and a prosthesis (not shown) is placed within the upper portion 128 of the previously prepared channel 98. The remaining space within this upper portion 128 is then filled with bone cement, which cannot flow past the bone plug 10, which is now in its partly expanded condition, with various surface held against the channel 96, as discussed in detail above in reference to FIG. 8.

While the hole 94 within the actuator 12 has been described as having internal threads, it is understood that thee actuator 12 may be fabricated without such threads, with threads subsequently being formed by thread forming surfaces on the distal portion 92 of the rod 88. In this context, thread forming surfaces include both surfaces which form threads by compression of material and surfaces which primarily cut threads by removal of material.

While the present invention has been described in its preferred forms or embodiments with some degree of particularity, it is understood that this description has been given only by way of example and that numerous changes in the details of construction, fabrication, and use, including changes in the combination and arrangement of parts, may be made without departing from the spirit and scope of the invention.

I claim:

1. A bone plug for plugging a channel within a bone to stop a flow of bone cement through said channel, wherein said bone plug comprises:

a plurality of flexible beams, extending around a periphery of said bone plug in a longitudinal direction within a central portion of said bone plug between first and second end portions of said bone plug, wherein said plurality of flexible beams includes an outer layer of flexible beams and an inner layer of flexible beams, wherein said inner and outer layers of flexible beams each extend around said periphery of said bone plug, wherein said inner layer of flexible beams extends under said outer layer of flexible beams, and wherein a center of each flexible beam within said inner layer of flexible beams extends beneath a gap between adjacent flexible beams within said outer layer of flexible beams;

an actuator movable between a disengaged position and an engaged position, wherein movement of said actuator from said disengaged position to said engaged position applies a compressive force acting between opposite ends of each flexible beam within said plurality of flexible beams, causing said flexible beam within said first plurality of flexible beams to buckle outward; and a latch holding said actuator in said engaged position.

2. The bone plug of claim 1, wherein said plurality of flexible beams includes a second plurality of flexible beams, and each flexible beam in said second plurality of flexible beams includes a wide groove extending transversely across an outer surface of said flexible beam near an end of said flexible beam.

3. A bone plug for plugging a channel within a bone to stop a flow of bone cement through said channel, wherein said bone plug comprises:

a plurality of flexible beams extending around a periphery of said bone plug in a longitudinal direction within a central portion of said bone plug between first and second end portions of said bone plug;

an actuator movable between a disengaged position and an engaged position, wherein movement of said actuator from said disengaged position to said engaged position applies a compressive force acting between opposite ends of each flexible beam within said plurality of flexible beams, causing said flexible beam within said first plurality of flexible beams to buckle outward;

a latch holding said actuator in said engaged position;

an outer sleeve having a central portion divided into an outer layer of flexible beams; and an inner sleeve, within said outer sleeve, having a central portion divided into an inner layer of flexible beams, wherein each flexible beam within said inner layer of flexible beams extends in said longitudinal direction, wherein movement of said actuator from said disengaged position to said engaged position applies a first compressive force acting through said outer layer of flexible beams between opposite ends of said outer sleeve; and a second compressive force acting through said inner layer of flexible beams between opposite ends of said inner sleeve, wherein said inner and outer layers of flexible beams include equal numbers of evenly spaced flexible beams, and wherein said inner and outer cylinders are held in a rotational relationship with one another causing a center of each flexible beam within said inner layer of flexible beams extends beneath a gap between adjacent flexible beams within said outer layer of flexible beams.

4. The bone plug of claim 3, wherein each flexible beam in said inner layer of flexible beams includes a section forming an edge extending transversely across said flexible beam and extending outwardly when said beam is buckled by movement of said actuator into said engaged position and a groove extending transversely across said flexible beam adjacent said groove.

5. The bone plug of claim 4, wherein said inner layer of flexible beams includes a first plurality of flexible beams having said edge offset toward said first end portion of said bone plug and a second plurality of flexible beams having said edge offset toward said second end portion of said bone plug.

6. The bone plug of claim 4, wherein
said groove is a narrow groove extending along an outer surface of said flexible beam, and
said edge is formed by an intersection of a surface forming a side of said groove and said outer surface of said flexible beam.

7. The bone plug of claim 4, wherein said groove is a wide groove extending along an inner surface of said flexible beam, and
said edge is formed along a rib extending along an outer surface of said flexible beam.

8. The bone plug of claim 3, wherein each flexible beam in said outer layer of flexible beams includes a central section having reduced thickness.

9. The bone plug of claim 3, wherein each flexible beam in said outer layer of flexible beams includes a wide groove extending transversely across an outer surface of said flexible beam near an end of said flexible beam.

10. A bone plug for plugging a channel within a bone to stop a flow of bone cement through said channel, wherein said bone plug comprises:

a plurality of flexible beams extending around a periphery of said bone plug in a longitudinal direction within a central portion of said bone plug between first and second end portions of said bone plug, wherein said plurality of flexible beams includes a first plurality of flexible beams, and wherein each flexible beam within said first plurality of flexible beams includes a section forming an edge extending transversely across said flexible beam along an outer surface of said flexible beam and extending outwardly when said beam is buckled by movement of said actuator into said engaged position and a groove extending transversely across said flexible beam adjacent said edge;

an actuator movable between a disengaged position and an engaged position, wherein movement of said actuator from said disengaged position to said engaged position applies a compressive force acting between opposite ends of each flexible beam within said plurality of flexible beams, causing said flexible beam within said first plurality of flexible beams to buckle outward; and a latch holding said actuator in said engaged position.

11. The bone plug of claim 10, wherein said first plurality of flexible beams includes a first number of flexible beams having said edge offset toward said first end portion of said bone plug and a second plurality of flexible beams having said edge offset toward said second end portion of said bone plug.

12. The bone plug of claim 10, wherein
said groove is a narrow groove extending along an outer surface of said flexible beam, and
said edge is formed by an intersection of a surface forming a side of said groove and said outer surface of said flexible beam.

13. The bone plug of claim 10, wherein said groove is a wide groove extending along an inner surface of said flexible beam, and
said edge is formed along a rib extending along an outer surface of said flexible beam.

14. A bone plug for plugging a channel within a bone to stop a flow of bone cement through said channel, wherein said bone plug comprises:

a plurality of flexible beams extending around a periphery of said bone plug in a longitudinal direction within a central portion of said bone plug between first and second end portions of said bone plug;

an actuator movable between a disengaged position and an engaged position, wherein movement of said actuator from said disengaged position to said engaged position applies a compressive force acting between opposite ends of each flexible beam within said plurality of flexible beams, causing said flexible beam within said first plurality of flexible beams to buckle outward, wherein said actuator includes an outward-extending portion applying said compressive force to an end of each flexible beam within said plurality of flexible beams within said first end portion of said bone plug;

a latch holding said actuator in said engaged position, wherein said latch, holding said actuator in said engaged position, applies a compressive force to an end of each flexible beam within said plurality of flexible beams within said plurality of flexible beans within said second end portion of said bone plug;

an outer sleeve having a central portion divided into an outer layer of flexible beams within said plurality of flexible beams, wherein said outward extending portion of said actuator applies a compressive force to a first end of said outer sleeve as said actuator is moved from said disengaged position to said engaged position, wherein said latch extends inward from a second end of said outer sleeve, opposite said first end of said outer sleeve, to engage said actuator; and an inner sleeve having a central portion divided into an inner layer of flexible beams within said plurality of flexible beams, wherein said inner sleeve extends within said outer sleeve and between said outward extending portion of said actuator and said latch extending inward.

15. Apparatus for plugging a channel within a bone to stop a flow of bone cement through said channel, wherein said apparatus comprises:

a bone plug including a plurality of flexible beams extending around a periphery of said bone plug in a longitudinal direction within a central portion of said bone plug between first and second end portions of said bone plug, an actuator movable between a disengaged position and an engaged position, wherein movement of said actuator from said disengaged position to said engaged position applies a compressive force acting between opposite ends of each flexible beam within said plurality of flexible beams, causing said flexible beam within said first plurality of flexible beams to buckle outward, and a latch holding said actuator in said engaged position, wherein a proximal end of said actuator includes an internally threaded hole; and an insertion tool including a frame and a rod, movable within said frame, removably attached to said actuator, wherein said rod moves said actuator in a first direction from said disengaged position to said engaged position, with said second end portion of said bone plug held in contact with said frame, before releasing said actuator, wherein said frame has a tubular structure slidably mounting said rod, wherein said tubular structure includes a restraining surface stopping motion of said actuator in said first direction past said engaged position, wherein said rod is moved from said disengaged position to said engaged position by an application of a first level of force to said rod in said first direction, wherein said rod is released from said actuator by an application of a level of force beyond said first level of force to said rod in said first direction, wherein a distal end of said rod includes an externally threaded shaft, wherein said rod is attached to said actuator with said externally threaded shaft engaging said internally threaded hole, and wherein said rod is released from said actuator by stripping threads within said internally threaded hole.

16. Apparatus for plugging a channel within a bone to stop a flow of bone cement through said channel, wherein said apparatus comprises:

a bone plug including a plurality of flexible beams extending around a periphery of said bone plug in a longitudinal direction within a central portion of said bone plug between first and second end portions of said bone plug, an actuator movable between a disengaged position and an engaged position, wherein movement of said actuator from said disengaged position to said engaged position applies a compressive force acting between opposite ends of each flexible beam within said plurality of flexible beams, causing said flexible beam within said first plurality of flexible beams to buckle outward, and a latch holding said actuator in said engaged position wherein a proximal end of said actuator includes a hole;

an insertion tool including a frame and a rod, movable within said frame, removably attached to said actuator, wherein said rod moves said actuator in a first direction from said disengaged position to said engaged position, with said second end portion of said bone plug held in contact with said frame, before releasing said actuator, wherein said frame has a tubular structure slidably mounting said rod, wherein said tubular structure includes a restraining surface stopping motion of said actuator in said first direction past said engaged position, wherein said rod is moved from said disengaged position to said engaged position by an application of a first level of force to said rod in said first direction, and wherein said rod is released from said actuator by an application of a level of force beyond said first level of force to said rod in said first direction, wherein a distal end of said rod includes a shaft with thread-forming screw threads, wherein said rod is attached to said actuator with said shaft engaging said hole and forming screw threads within said hole, and wherein said rod is released from said actuator by stripping said screw threads formed within said hole.

17. A process for plugging a channel within a bone at a predetermined level within said channel to stop a flow of bone cement through said channel, wherein said process comprises:

attaching a bone plug to a distal tip of an insertion tool, wherein attaching said bone plug to said distal tip of said insertion tool includes engaging screw threads on a distal tip of a rod within said insertion tool with a hole in a proximal end of an actuator within said bone plug;

inserting said bone plug attached to said insertion tool to said predetermined level within said channel;

pulling said rod within said insertion tool to cause said bone plug to expand within said channel into contact with said channel, wherein pulling said rod within said insertion tool causes said actuator, attached to said rod, to move between a disengaged position and an engaged position, wherein movement of said actuator between said disengaged position and said engaged position applies a compressive force between opposite ends of flexible beams extending around a periphery of said bone plug, causing said flexible beams to buckle outward into contact with said channel, and wherein an external structure of said bone plug, extending outward from said actuator, is held in place by a channel of said insertion tool as said rod is pulled within said channel of said insertion tool;

releasing said bone plug from said insertion tool, wherein releasing said bone plug from said insertion tool includes moving said actuator against a restraining surface of said channel of said insertion tool, and pulling said distal tip of said rod out of said hole in said proximal end of said actuator while stripping threads within said hole in said proximal end of said actuator with said actuator held against said restraining surface of said channel of said insertion tool; and withdrawing said insertion tool from said channel.

* * * * *